US011385213B2

(12) United States Patent
Jouper

(10) Patent No.: US 11,385,213 B2
(45) Date of Patent: Jul. 12, 2022

(54) STORAGE BIN VOLUME SENSOR WITH VOC SENSING SAFETY FEATURE

(71) Applicant: Astronics Advanced Electronic Systems Corp., Kirkland, WA (US)

(72) Inventor: Jeffrey A. Jouper, Newcastle, WA (US)

(73) Assignee: Astronics Advanced Electronic Systems Corp., Kirkland, WA (US)

(*) Notice: Subject to any disclaimer, the term of this patent is extended or adjusted under 35 U.S.C. 154(b) by 0 days.

(21) Appl. No.: 15/978,550

(22) Filed: May 14, 2018

(65) Prior Publication Data

US 2018/0335413 A1 Nov. 22, 2018

Related U.S. Application Data

(60) Provisional application No. 62/507,423, filed on May 17, 2017.

(51) Int. Cl.
*G01N 33/00* (2006.01)
*G01S 17/08* (2006.01)
(Continued)

(52) U.S. Cl.
CPC ......... *G01N 33/0047* (2013.01); *G01F 17/00* (2013.01); *G01S 17/08* (2013.01); *G01S 17/87* (2013.01)

(58) Field of Classification Search
CPC ..... G01N 33/0047; G01F 17/00; G01S 17/08; G01S 17/87
(Continued)

(56) References Cited

U.S. PATENT DOCUMENTS 6,447,731 B1 9/2002 Sun et al.
6,491,254 B1 * 12/2002 Walkinshaw ............ A62C 3/08
244/118.5
(Continued)

FOREIGN PATENT DOCUMENTS

CA 2986085 12/2016
EP 2178035 A1 4/2010
(Continued)

OTHER PUBLICATIONS

"Lithium batteries with more than 100 watt hours" (www.tsa.gov/travel/security-screening/whatcanibring/items/lithium-batteries-more-100-watt-hours. Sep. 16, 2020).*
(Continued)

*Primary Examiner* — Nimeshkumar D Patel
*Assistant Examiner* — Jean F Morello
(74) *Attorney, Agent, or Firm* — Wiggin and Dana LLP; Rikesh P. Patel; Gregory S. Rosenblatt

(57) ABSTRACT

Operation of an overhead storage bin sensor used to monitor the volume consumed within the bin including a VOC sensor to monitor for material that may become overheated within the bin such as lithium ion batteries in electronics products is provided. Currently, fire or smoke detectors are not integrated into the storage bins leaving this area vulnerable to developing fires and outgassing of electronic components often stored by passengers. Early detection of such events can prevent propagation of fire on board an aircraft by rapidly reporting the event and giving the location of the event. The system described leverages other patents applied for including a wireless sensor network and storage volume sensors. The sensor monitors for outgassing of materials or smoldering material by monitoring the air quality within the bin space.

17 Claims, 5 Drawing Sheets

(51) Int. Cl.
*G01F 17/00* (2006.01)
*G01S 17/87* (2020.01)

(58) Field of Classification Search
USPC .......................................................... 73/23.31
See application file for complete search history.

(56) References Cited

U.S. PATENT DOCUMENTS

| | | | | |
|---|---|---|---|---|
| 6,958,689 | B2* | 10/2005 | Anderson | A62C 35/08 |
| | | | | 340/525 |
| 8,232,884 | B2* | 7/2012 | Pattok | G08B 3/10 |
| | | | | 340/539.26 |
| 10,295,457 | B1* | 5/2019 | Ocheltree | G01N 33/0031 |
| 10,399,409 | B2* | 9/2019 | Wang | B60H 1/008 |
| 2012/0168184 | A1* | 7/2012 | Enk, Sr. | A62C 37/44 |
| | | | | 169/14 |
| 2012/0192908 | A1* | 8/2012 | Kline | B64C 1/38 |
| | | | | 136/205 |
| 2013/0002443 | A1 | 1/2013 | Breed et al. | |
| 2013/0071290 | A1 | 3/2013 | Goldstein et al. | |
| 2013/0299000 | A1 | 11/2013 | Gillette, II | |
| 2013/0338857 | A1* | 12/2013 | Sampigethaya | G06F 17/00 |
| | | | | 701/3 |
| 2015/0241209 | A1 | 8/2015 | Jouper et al. | |
| 2015/0303723 | A1* | 10/2015 | Raghavan | G01N 33/0036 |
| | | | | 320/107 |
| 2015/0377824 | A1* | 12/2015 | Ruhl | G01N 33/004 |
| | | | | 204/424 |
| 2016/0015278 | A1 | 1/2016 | Campo et al. | |
| 2017/0255855 | A1 | 9/2017 | Jouper | |

FOREIGN PATENT DOCUMENTS

| | | |
|---|---|---|
| JP | H08751 A | 1/1996 |
| JP | 2012/529097 A | 11/2012 |
| JP | 2017-36029 A | 2/2017 |
| WO | WO 2015053793 | 4/2015 |
| WO | 2016/189420 A1 | 12/2016 |

OTHER PUBLICATIONS

PCT Search Report and Written Opinion in related application PCT/US18/32951, dated Sep. 13, 2018, 11 pages.

European Patent Office, European Search Report and Provisional Opinion Accompanying the Partial Search Result, for EP 18803284, dated Dec. 11, 2020, p. 7.

Japan Patent Office, Translation of Office Action, for JP Application No. 2019-563404, dated Dec. 25, 2020, p. 5.

* cited by examiner

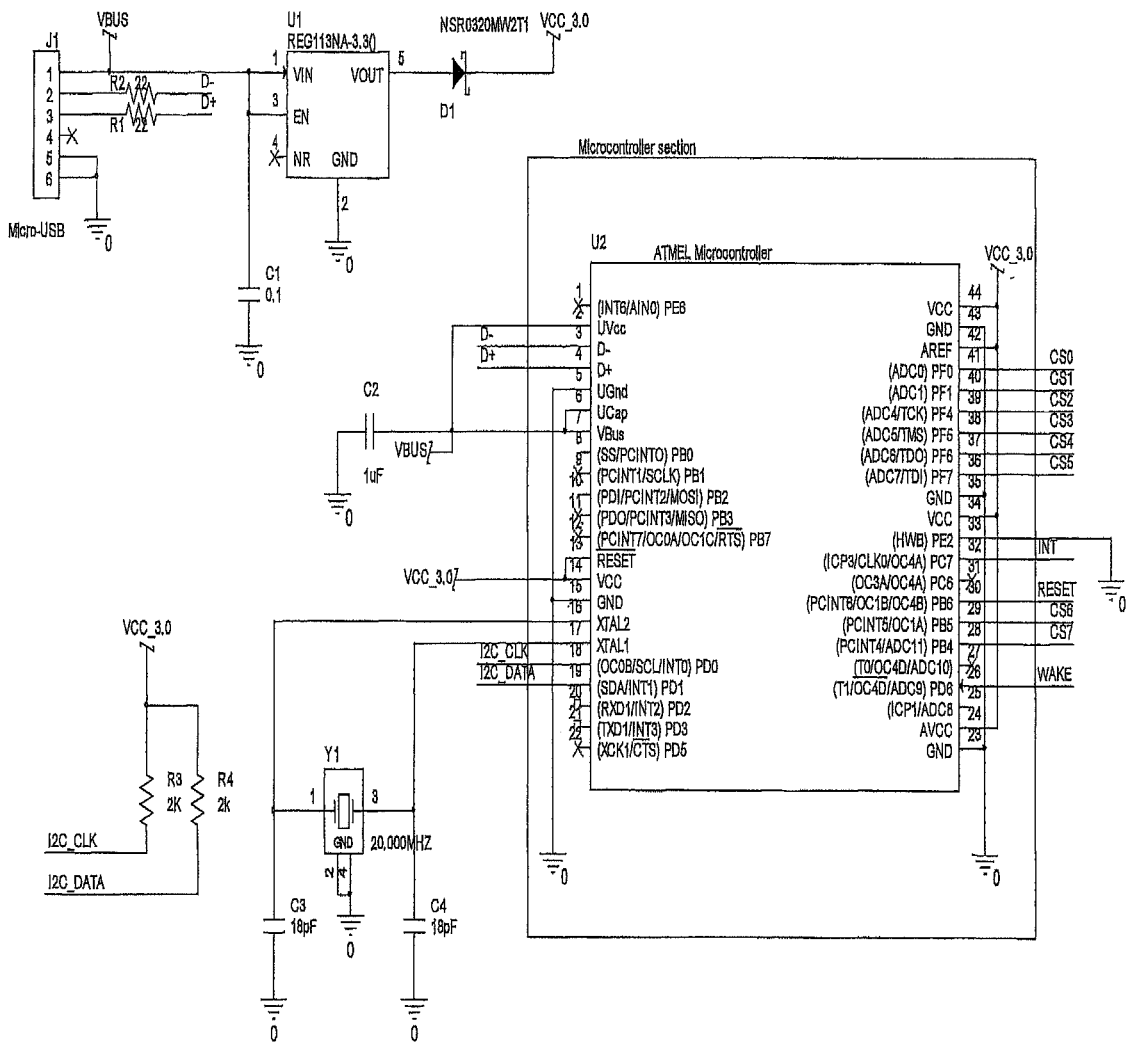
FIG. 3a- Schematic

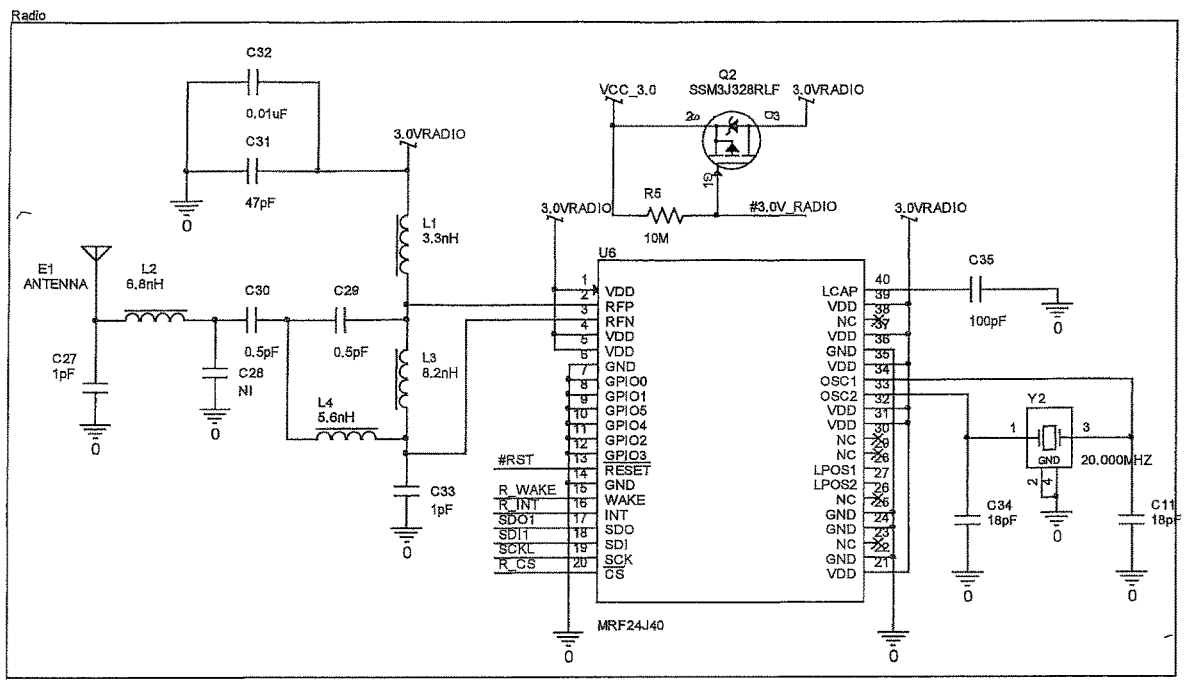
Figure 3b - Radio

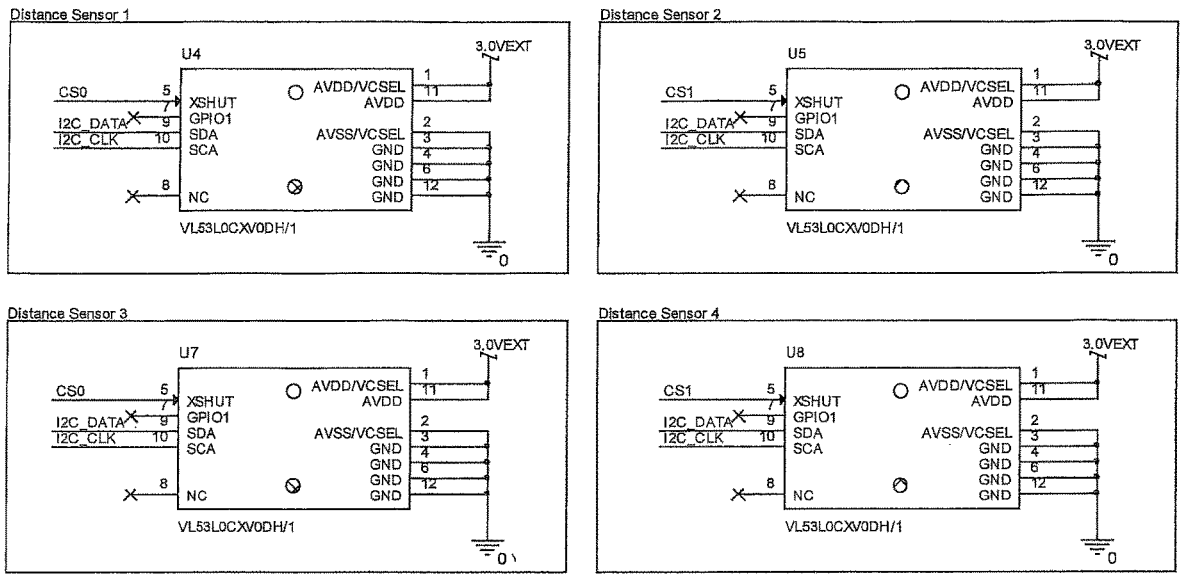
Figure 3c – ToF Sensors

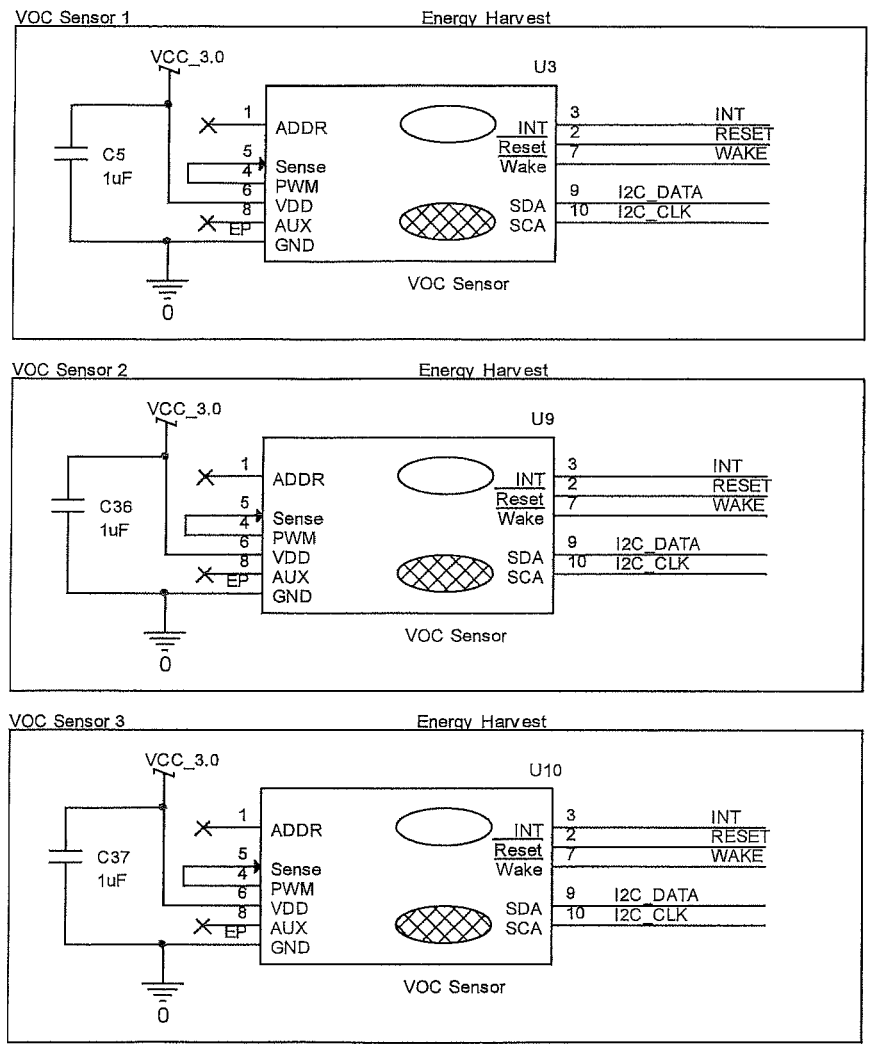
Figure 3d – VOC Sensor

STORAGE BIN VOLUME SENSOR WITH VOC SENSING SAFETY FEATURE

BACKGROUND OF THE DISCLOSURE

Storage bins are ubiquitous in the passenger cabin of commercial aircraft. The storage bins are located above the passenger seats and hold all types of materials carried onto the aircraft by passengers. Sensors to detect the volume of material placed in storage bins are disclosed in United States Patent Application Publication No. US 2015/0241209 A1, "Apparatus and Method to Monitor the Occupied Volume within a Fixed or Variable Volume," by Jouper et al. and United States Patent Application Publication No. 2017/0255855 A1, "Network System for Autonomous Data Collection," by Jouper. US 2015/0241209 A1 and US 2017/0255855 are both incorporated by reference herein in their entireties.

Current bin sensors sense items occupying a portion of the storage bin volume and determine the volume occupied within the bin. The bin sensors report that information to an external network for annunciation to the cabin crew, ground crew and/or a data collection system.

While bin volume occupancy is valuable information, there exists a need to not only monitor the bin volume consumed, but status of the material stored. More specifically, materials such as lithium batteries and any device containing a lithium battery, large storage capacitor and small electronics can cause problems on-board aircraft. Lithium batteries in particular have been a source of several in-flight incidences, such as outgassing, electronic odors and spontaneous fires. The storage bin presents a unique situation where laptop computers, tablets, smartphones and other electronics are often packaged internal to the carry-on baggage, briefcases and other holders. Each of these holders present fuel to a fire should it begin within the storage bin area.

Current fire or smoke detectors are not integrated into storage bins, leaving these closed compartments particularly vulnerable.

It would be desirable, therefore, to provide a device and method for monitoring the contents of a storage bin.

It would be yet further desirable to provide a storage bin sensor, with a volatile organic compound ("VOC") sensing feature.

BRIEF SUMMARY OF THE DISCLOSURE

Disclosed is an overhead storage bin sensor for use in monitoring the volume occupied within a storage bin. The sensor is particularly suited as a VOC sensor to monitor for materials or items that may become overheated within the storage bin, such as lithium-ion batteries in electronic products.

The VOC sensor is configured for early detection of outgassing, odors and fire from electronic components often stored by passengers. Early detection may allow for rapid response onboard the aircraft, prevent propagation of an onboard fire or gas emergency via rapid reporting and flagging of the event, and even avoid emergency landings.

In accordance with the invention, VOC sensors monitor for outgassing of materials or smoldering material by monitoring air quality within storage bin space.

BRIEF DESCRIPTION OF THE DRAWINGS

The foregoing summary, preferred embodiments and other aspects of the subject matter of the present disclosure will be best understood with reference to a detailed description of specific embodiments, which follows, when read in conjunction with the accompanying drawings, in which:

FIG. 3A is a schematic diagram in accordance with an embodiment.

FIG. 3B is a schematic diagram of a radio interface in accordance with an embodiment.

FIG. 3C is a schematic diagram of a ToF sensor in accordance with an embodiment.

FIG. 3D is a schematic diagram of a VOC sensor in accordance with an embodiment.

Like reference numbers and designations in the various drawings indicate like elements. Arrows in the schematic drawings should be understood to represent logic pathways that are generally indicative of the flow direction of information or logic, and that such arrows do not necessarily represent traditional electrical pathways.

DETAILED DESCRIPTION OF THE DISCLOSURE

To mitigate a fire or chemical leak incident, a system that can detect such issues early and signify to the flight crew the event and the location of the event within the bin assembly may mitigate the propagation of fire and allow the flight crew time to react to the situation, rather than waiting for the fire to present external to the storage bin.

Figure 1:
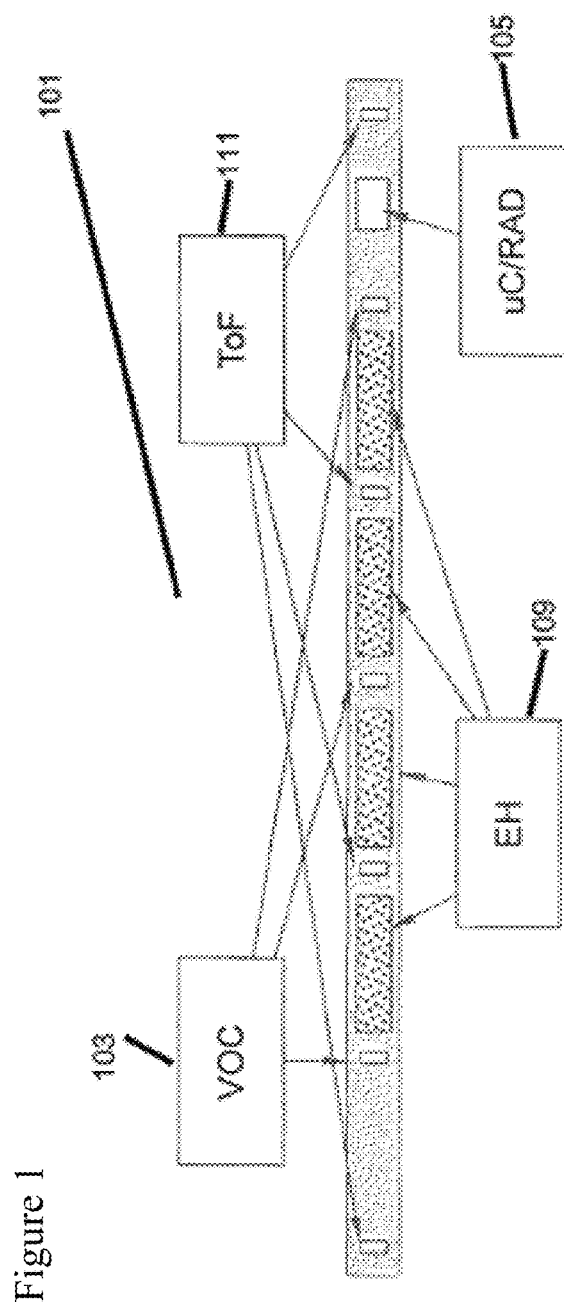
FIG. 1 is a sensor assembly in accordance with an embodiment.

FIG. 1 depicts a sensor assembly 101 showing sensors for Volatile Organic Compounds (VOC) 103, microcontroller (uC) 105, Radio for sending data (RAD) 107, Energy Harvester(EH) 109 in cases where needed, distance sensors for the bin volume 111 (Time of Flight, ToF).

In an embodiment, distance from the top of the bin to a reflective surface (such as a bottom of the bin, or material stored in the bottom of the bin) and then back to the top of the bin where the sensor resides, represents a distance as measured by a time of flight sensor. For example, a time of flight sensor measures the time it takes for light to propagate from the sensor, to the reflective surface, and then back again. In a further example, this distance is divided in two to measure the distance from the sensor to the surface, and measures the speed of light. Thus, an amount of space available in a storage bin is calculated by taking the distance measured by a reference measurement with an empty bin.

The volume/distance sensors are a time of flight sensor or any other appropriate sensor used to measure distance. For example, such volume/distance sensors may be chosen from sensors in the Infrared (IR) or Laser (sub-IR) frequencies. These sensors are ideally -suited based on small physical size and robustness. Multiple sensors are used to break the storage area into segments based on the bin length and depth, measuring the distance from the top of the bin to the bottom of the bin. For example, storage bin length and depth may be measured, and based on both length and depth, may be divided into a predetermined number of segments, with each segments receiving at least one sensor. To monitor for smoke or venting of lithium batteries or other devices, a number of VOC sensors are used to continuously or on a pre-programmed interval, monitor the air quality within the storage bin and annunciate through the sensor network if a significant event happens. As discussed herein, significant events may include any worrisome, dangerous or otherwise elevated level of VOCs, outgassing, fire or any other form of combustion.

Volume Sensing

Using an initial measurement as a reference, each distance sensor measures the distance from the top of the bin to the material added as passengers load the aircraft. The microcontroller sets the time frame from measurement to measurement and calculates the percentage of use based on the reference taken during initialization of the sensor and the depth measurements. This is displayed for the flight crew at a centralized panel displaying the layout of the aircraft, storage bin location and percentage of used space or space available. This allows the crew early warning of the bin space volume available as the passengers load the overhead storage bins. By monitoring space volume, the crew may mitigate loading time increases by removing excess baggage from the interior of the aircraft to the cargo hold and locate bin space available. This system can report, at an instant, locations and relative volume available.

Air Quality Sensing

Air quality sensing is used to monitor events such as outgassing of vapors from lithium batteries, capacitors and other energy storage devices. In general, energy storage devices present a unique issue in that there are self-power issues. Lithium batteries have shown a propensity to self-ignite due to impurities in the chemicals used to build the battery. Because the lithium battery stores energy for consumption by devices attached to it, such as laptop computers, tablet computers or cellular phones, the lithium battery becomes a self-starting and self-perpetuating potential for an overheating, outgassing, or combustible event. This event in hidden spaces such as the storage bin may not present itself to the passengers or cabin crew until a fire begins to exit the storage bin itself. This would then have involved some, if not all, of the materials in that bin to a propagating fire. Early detection and exact locating of the event is particularly advantage and an aid in the safety of flight.

In an embodiment, annunciation of the event may be local to the storage bin such as a light emitting diode (LED) indicator, on a remote panel, display, hand held device or overhead projection device. The projection device may be located above the bin opposite the location of the bin with the event. The projector could then project a RED or other appropriate color display to the front of the bin at issue, thereby quickly signifying to the cabin crew the location of a significant event. In a further embodiment, annunciation may be hyper-localized, such that the predetermined-segments within a storage bin may each contain a corresponding LED indicator, which may then be located above the segment and configured to display an alarm or signify a location upon occurrence of a significant event.

Additionally, this sensor could be a standalone device used to monitor spaces and places where events of outgassing or fire would be difficult to spot visually, such as in the overhead, behind panels, sidewalls, under seats, in the galley, closets, flight deck or cabin crew rest areas. A standalone sensor may be a single or multiple VOC sensor, a microcontroller, radio, energy storage device or energy harvester to operate the sensors. Other sensors such as IR (heat sensor) could also be used in conjunction with the VOC sensor to detect and annunciate a pre- or post-ignition fire. Each of these sensors aid the cabin crew in identifying possible fires before they propagate. Decreasing time from event to detection can mean the saving of lives and equipment aboard aircraft.

Function Description

The sensor is preferably located in the top of the overhead storage bin. Locating here allows for continuous measurement of the storage volume used. Additionally, vapors tend to rise from faulting devices. Other placements may work, however, the top is preferred for obvious reasons.

FIG. 1 graphically describes four ToF sensors with three VOC sensors and the MicroController (uC) circuitry, including the radio as well as energy harvesting using solar cells or small battery cells. The ToF sensor measures a bin empty distance from the sensor to the bottom of the bin and back. A laser sensor is used for speed, accuracy and immunity to ambient light. Generally, choosing a light frequency wavelength that is not included in sun light is advantageous, in that ambient light does not disrupt the measurement cycle.

The uC is the heart of the sensor. It controls the radio, sensor measurements, timing of measurement and radio transmissions. The uC communicates with each sensor across an Inter-Integrated Circuit (I2C) interface for initialization of each sensor as well as gathering measurement data, whether it be ToF or VOC data. Each sensor is individually enabled and communicates with the uC.

Volume measurements are done on a periodic basis, such as once per second or once per 10 seconds, or any other suitable period. The volume measurement is generally only done while the aircraft is boarding. That is, this data is only relevant during the loading process of the aircraft. The VOC sensor on the other hand, is set up during initialization with a pre-programmed threshold. The threshold represents a minimum VOC level for detection and annunciation. The threshold level is set above the ambient amount of VOC seen in the environment the sensor is in. In the cabin of a commercial passenger aircraft, an exemplary ambient of VOC concentration is 300 parts per billion and an exemplary threshold VOC concentration to trigger the alarm 500 parts per billion.

The VOC sensor is set to measure periodically, such as once every 250-60000 milliseconds. The minimum time of each measurement for current sensors is 250 milliseconds. Delays of longer than 60000 milliseconds (60 seconds) between measurements may delay the sensing of an event in relative real time. Oversampling at time intervals of less than 250 mSec will use more power and decrease battery life of the system. The limitations of the upper and lower boundaries of sample rate may be exceeded depending on power available and other system requirements.

When the pre-programmed VOC level is exceeded, an interrupt is sent to the uC from the VOC sensor. This interrupt signifies that an event has triggered the sensor by exceeding the threshold. The uC processes this event and sends a warning through the radio to an external receiver or the uC enables a local light or display to indicate that an event inside that stowage bin has occurred. This display or the remote display guides the cabin crew to the location of the event for further action.

Figure 2:
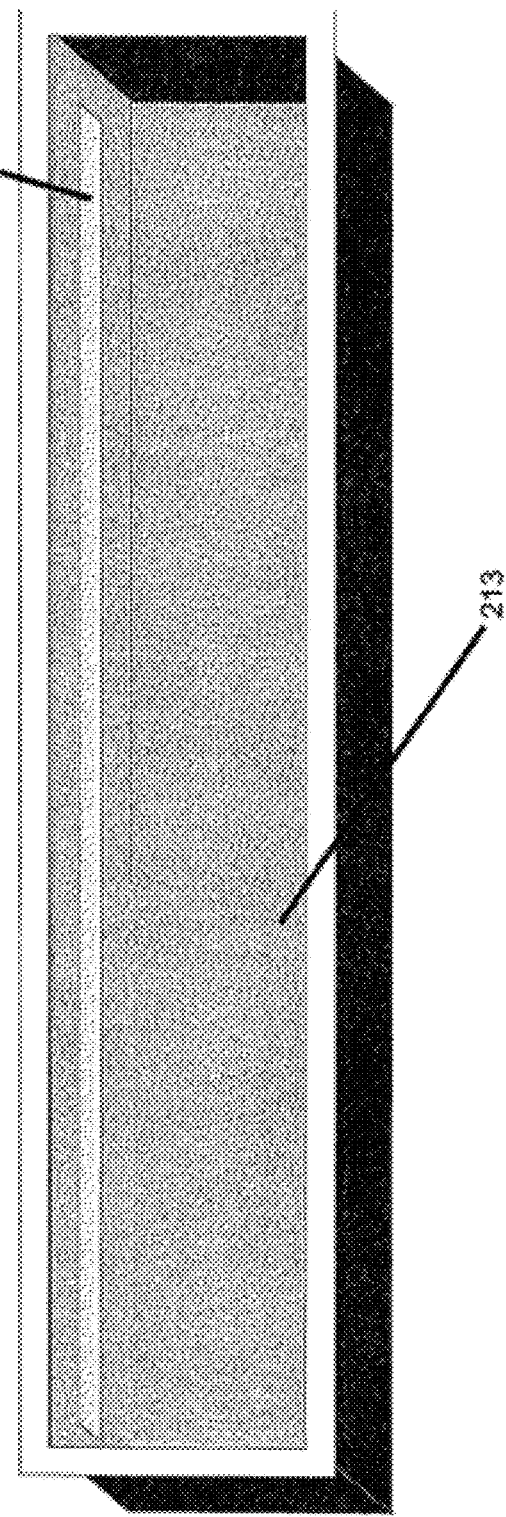
FIG. 2 is a diagram of an embodiment of the sensor assembly within a storage bin.

FIG. 2 illustrates an embodiment of the sensor assembly within a storage bin. As shown, the sensor may be located in an interior top portion of the storage bin. Alternatively, other suitable locations may be utilized, such as interior bottom portion, or side portions, of the storage bin.

FIG. 3A-3D are the schematics of the sensor system including the uC, radio, VOC sensor and ToF sensors.

FIG. 3A illstrates the microcontroller/radio combination. This could be a single chip solution where the uC and the radio are combined, or a discrete solution where the radio and uC are separate with a communication bus between the microcontroller and the radio. J1 is a USB programming port for loading software to cooperatively operate the uC, radio and sensors. Regulator U1 provides a regulated 3VDC supply from the USB connector during load of the appropriate code. U2 is a 32 bit uC with communication busses to the radio and the sensors. Chip select outputs of the microcontroller, CS0-CS7 allow the uC to address each sensor individually by setting this interface to a logic 1. Communication to the sensors takes place across the I2C interface, as all sensors share a common bus, the chip select interfaces are used to determine which sensor is to be addressed at any given time. Y1 is the oscillator to control the frequency of operation for the uC.

FIG. 3B is the radio interface. This is a 2.4 GHz radio with E1 being a matched antenna for the radio frequency. The associated components between the RFP/RFN outputs of the radio and the antenna are an impedance matching network to provide the highest gain of the antenna for the least energy applied by the radio U6. Y2 sets the frequency of operation for the radio. Communication from the uC over the Serial Peripheral Interface (SPI) bus provides control of the radio, transfer of data from the uC to the radio and a command set to send radio information wirelessly.

FIG. 3C illustrates the ToF sensors used to measure the distance from the sensor to the bin floor or the material located in the bin. A reference is taken when the bin is empty, in order to calculate the percentage used. Continuous measurements are taken thereafter and compared with the reference, to calculate percentage of space consumed below each of the sensors. The measurements of each sensor are averaged to become the total volume consumed. The value calculated for each segment as well as the total value can be reported to the display to show available space, space consumed and area within the bin that space is available.

FIG. 3D illustrates the VOC sensors. These sensors are controlled by the uC to measure the CO2 and Volatile Organic Compound values within the bin space. The value read is compared to a threshold and if it exceeds the threshold, will alert the cabin crew of that event. The uC initiates the measurement, compares the result to the threshold and if the value is in excess of that limit, sends an alarm through the radio and in turn to the display either local to or remote of the bin signifying which bin and bin segment the event is located.

It should be understood that various components of the disclosed subject matter may communicate with one another in various manners. For instance, components may communicate with one another via a wire or, alternatively, wirelessly and by electrical signals or via digital information.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A sensor assembly for use in a plurality of storage bins located in a passenger cabin of a commercial aircraft, the sensor assembly comprising:
a plurality of Volatile Organic Compound (VOC) sensors configured to sense a VOC concentration level of each storage bin;
a plurality of volume sensors configured to periodically measure an unoccupied volume of each storage bin, wherein the plurality of VOC sensors and the plurality of volume sensors are alternately disposed along the sensor assembly; and
a microcontroller configured to communicate with the volume sensors and VOC sensors within each storage bin, the microcontroller programmed with a threshold VOC concentration level and configured to compare the sensed VOC concentration level with the threshold level and output an alert when the sensed VOC concentration level in one or more of the storage bins exceeds the threshold level;
wherein the microcontroller is further configured to transmit the alert to a central location on the aircraft, the alert being at least one of an audio or visual alert to indicate that the sensed VOC concentration level in the one or more of the storage bins has exceeded the threshold level.

2. A sensor assembly comprising:
a microcontroller; and
a Volatile Organic Compound (VOC) sensor configured to sense a VOC concentration level in a storage bin and to communicate the sensed level to the microcontroller;
wherein the microcontroller is programmed with a threshold VOC concentration level and configured to compare the sensed VOC concentration level with the threshold level and output an alert when the sensed VOC concentration level of the storage bin exceeds the threshold level;
wherein the microcontroller is further configured to transmit the alert to an external receiver, the alert being at least one of an audio or visual alert to indicate that the sensed VOC concentration level in the one or more of the storage bins has exceeded the threshold level, and
wherein when an ambient VOC concentration level is 300 parts per billion, the threshold VOC concentration level to trigger the alert is 500 parts per billion.

3. The sensor assembly of claim 2, wherein the sensor assembly further comprises a distance sensor configured to measure the distance from the distance sensor to an opposed reflective surface within the storage bin, and wherein the distance sensor operates on an infrared frequency.

4. The sensor assembly of claim 3, wherein the distance sensor is one of a plurality of distance sensors, the plurality of distance sensors mounted to an internal top surface of the storage bin and spaced apart to divide the storage bin into a plurality of segments.

5. The sensor assembly of claim 4, wherein the segments are divided based on a length and depth of the storage bin length and depth.

6. The sensor assembly of claim 4, wherein the distance sensor is configured to measure distance from a top of the storage bin to a bottom of the storage bin.

7. The sensor assembly of claim 2, wherein the VOC sensor is configured to periodically monitor for smoke or venting.

8. The sensor assembly of claim 7 wherein the smoke or venting originates from lithium batteries.

9. The sensor assembly of claim 7 wherein the VOC sensor monitors air quality within a storage bin.

10. The sensor assembly of claim 9 wherein the VOC sensor annunciates a significant event.

11. The sensor assembly of claim 10 wherein the significant event is selected from the group consisting of an elevated level of VOC, outgassing, or fire.

12. The system of claim 2, wherein the sensor assembly further comprises a radio, wherein the radio transmits the audio alert via alarm signal data.

13. The system of claim 2, wherein the sensor assembly further comprises an energy harvester, wherein the energy harvester includes a solar cell or a small battery.

14. A method of sensing storage bin available volume and detecting a significant event, comprising:
- measuring an initial reference volume measurement of a storage bin;
- measuring, using a distance sensor, distance from a top of the storage bin to a top of loaded material;
- setting, using a microcontroller, a time frame for performing subsequent periodic measurement of distance using the distance sensor;
- calculating a percentage of use of storage bin volume based on the initial reference volume measurement and the subsequent measurement of distance;
- sensing a VOC level via a VOC sensor located in the storage bin;
- detecting, using the microcontroller, a significant event when the sensed VOC level exceeds a threshold level; and
- alerting, using at least one of an audio alert or visual alert, the significant event to an external receiver via the microcontroller.

15. The method of claim 14, further comprising displaying, on a display panel, storage bin location and percentage of used space within the storage bin at the location.

16. The method of claim 15, further comprising annunciating, via the VOC sensor, the significant event.

17. The method of claim 16, wherein the significant event is selected from the group consisting of an elevated level of VOC, outgassing, or fire.

* * * * *